(12) United States Patent
Kleinwaechter

(10) Patent No.: US 8,343,534 B2
(45) Date of Patent: Jan. 1, 2013

(54) TISSUE INCLUDING A VOLATILE RHINOLOGICAL COMPOSITION

(75) Inventor: Joerg Kleinwaechter, Hofheim Am Tanus (DE)

(73) Assignee: The Procter & Gamble Company, Cincinnati, OH (US)

( * ) Notice: Subject to any disclaimer, the term of this patent is extended or adjusted under 35 U.S.C. 154(b) by 1306 days.

(21) Appl. No.: 11/225,949

(22) Filed: Sep. 14, 2005

(65) Prior Publication Data

US 2006/0073195 A1 Apr. 6, 2006

Related U.S. Application Data

(63) Continuation-in-part of application No. 11/105,996, filed on Apr. 14, 2005.

(60) Provisional application No. 60/565,105, filed on Apr. 23, 2004.

(30) Foreign Application Priority Data

Feb. 28, 2005 (EP) .................................... 05004303

(51) Int. Cl.
*A61K 9/10* (2006.01)
*A61K 7/00* (2006.01)

(52) U.S. Cl. ......................... 424/443; 424/402; 424/404

(58) Field of Classification Search .................. None
See application file for complete search history.

(56) References Cited

U.S. PATENT DOCUMENTS

| | | | |
|---|---|---|---|
| 3,311,459 A | 3/1967 | Francis et al. | |
| 3,818,533 A | 6/1974 | Scheuer | |
| 4,338,876 A | 7/1982 | Norton | |
| 4,668,564 A | 5/1987 | Orchard | |
| 5,123,411 A | 6/1992 | Noziri | |
| 5,275,859 A | 1/1994 | Phillips et al. | |
| 5,451,404 A * | 9/1995 | Furman | 424/401 |
| 5,525,345 A | 6/1996 | Warner et al. | |
| 5,607,754 A | 3/1997 | Giles et al. | |
| 5,702,376 A | 12/1997 | Glaug et al. | |
| 5,720,966 A | 2/1998 | Ostendorf | |
| 5,830,487 A * | 11/1998 | Klofta et al. | 424/402 |
| 5,980,924 A * | 11/1999 | Yamazaki et al. | 424/402 |
| 6,238,682 B1 | 5/2001 | Klofta et al. | |
| 6,458,343 B1 | 10/2002 | Zeman et al. | |
| 6,586,652 B1 | 7/2003 | Roe et al. | |
| 6,592,884 B2 | 7/2003 | Hofmann et al. | |
| 6,602,387 B1 | 8/2003 | Loughran et al. | |
| 6,921,745 B2 | 7/2005 | Yamada | |
| 2002/0120014 A1* | 8/2002 | Surburg et al. | 514/715 |
| 2002/0174863 A1 | 11/2002 | Saric et al. | |
| 2003/0139291 A1 | 7/2003 | Qin | |
| 2003/0161802 A1 | 8/2003 | Flammer et al. | |
| 2004/0052828 A1 | 3/2004 | Hofmann et al. | |
| 2004/0081680 A1 | 4/2004 | Pesce et al. | |
| 2004/0086476 A1 | 5/2004 | Flammer et al. | |
| 2004/0132630 A1 | 7/2004 | Yamada et al. | |
| 2005/0027017 A1 | 2/2005 | Surburg et al. | |
| 2005/0136765 A1 | 6/2005 | Shannon | |

FOREIGN PATENT DOCUMENTS

| | | |
|---|---|---|
| EP | 0 370 600 A1 | 5/1990 |
| EP | 1 408 155 A | 4/2004 |
| EP | 1 408 155 A1 | 4/2004 |
| GB | 479671 | 2/1938 |
| GB | 672 254 A | 5/1952 |
| GB | 672254 | 5/1952 |
| JP | 60-101449 | 6/1985 |
| WO | WO 96/19204 | 6/1996 |
| WO | WO 99/45771 | 9/1999 |
| WO | WO 03/048654 A1 | 6/2003 |

OTHER PUBLICATIONS

May 2, 2008 Office Action for co-pending U.S. Appl. No. 11/225,905.

* cited by examiner

*Primary Examiner* — Daniel Sullivan
*Assistant Examiner* — Kyle Purdy
(74) *Attorney, Agent, or Firm* — Andrew A. Paul

(57) ABSTRACT

Tissues useful in providing fibrous tissue products for skin contact, such as facial tissue, bathroom tissue, disposable handkerchiefs which comprise a volatile rhinological effective composition for delivery to human skin.

12 Claims, No Drawings

TISSUE INCLUDING A VOLATILE RHINOLOGICAL COMPOSITION

CROSS REFERENCE TO RELATED APPLICATIONS

This application is a continuation-in-part application of U.S. application Ser. No. 11/105,996 filed Apr. 14, 2005, which claims benefit to U.S. Provisional Application Ser. No. 60/565,105 filed Apr. 23, 2004.

FIELD OF THE INVENTION

The present invention relates to tissues useful in providing fibrous tissue products for skin contact, such as facial tissue, bathroom tissue, disposable handkerchiefs which comprise a volatile rhinological effective composition for delivery to human skin.

BACKGROUND OF THE INVENTION

Fibrous tissues useful in providing tissue products for skin contact are most frequently simple paper tissues, which find extensive use in modem society and are well known in the art. They are sometimes called paper webs or sheets, tissues, tissue layers, paper plies or paper tissue webs, and products made there from, such as paper handkerchiefs, paper kitchen towels or bath tissues, toilet paper or facial tissues.

Paper tissues, or more generally fibrous tissues of the present context, are generally made by the layering of fibers, mostly cellulose fibers, in a wet form, onto a screen, with the addition of various additives or other ingredients, optionally including other, natural or synthetic fibers, followed by a drying step. Other process steps, before, during or after the above-mentioned paper tissue making steps are targeted at giving the desired properties to the tissue. Converting steps are aimed at creating a finished product from the tissue(s).

Products made from fibrous tissues can be made by the association of multiple layers of tissues, also called plies, or can comprise a single tissue layer (single ply products). Those plies can be combined and held together in multiple ways to form the finished product, for example by embossing of the multi-ply structure or/and by gluing. The finished products are herein referred to as paper tissue products or fibrous tissue products. Finished products made of more than one ply have internal tissue (or ply) surfaces, inwardly orientated, and two external surfaces, outwardly orientated.

It has long been recognized that important physical attributes of these paper tissue products are their strength and thickness/bulkiness, their softness and smoothness, and their absorbency. Softness and smoothness relate to the tactile sensation perceived by the consumer when holding a particular product, rubbing it across the skin, or crumpling it within the hands.

Relatively thick and yet soft disposable paper products, namely in the form of paper handkerchiefs, are known. For example, Tempo™, sold by The Procter & Gamble Company, is a multi-ply paper product experienced as thick and soft and having a caliper of about 0.3 mm. A high caliper conveys the idea of high dry and wet strength to the consumer. A high wet strength, also referred to as wet burst strength, in particular prevents tearing or bursting, which for a paper handkerchief in turn results in contamination of the user's hand with mucus or other body fluids.

A common way to enhance the smoothness of the tissue surface is to calender the material. Another way to improve the sensation of smoothness perceived by the users of paper tissue products, such as handkerchiefs, is to complement the composition of the tissue with some additives during the paper-making phase and/or during the converting phase. Those additives can have the effect of smoothening the tissue in a way that makes the user feel it more soft or smooth. Alternatively or additionally some additives have an effect on the skin of the user touching or using the paper tissue product, e.g. smoothening of the skin or hydration of the skin. These later effects are usually obtained through a partial transfer of the additives onto the skin during usage, thus prolonging the effect of the additives on the skin beyond the period of contact between the paper-tissue product and skin.

Smoothening lotions are usually of hydrophobic nature or contain hydrophobic compounds. Thus, the presence of the lotion at the surface of the paper tissue product can have adverse effects on the properties. For example, the masking of the hydrophilic tissue surface can reduce the absorbency or the speed of absorbency. Further, the lotion can migrate from the tissue surface into the structure making the tissue less hydrophilic and reducing the lotion available at the surface to deliver the smoothening benefits to the skin. Increasing the amount of lotion can in turn create an excess of lotion on the tissues creating a greasy feeling during use and further reducing the absorbency.

Even if such problems of the smoothening of the skin of users of tissue products are addressed there remain improvement aspects for tissue products, especially during high frequency usage conditions when a user suffers from a cold or allergy induced runny nose and breathing difficulties often together with other discomfort referred to as rhinological discomfort. Relieving, for example cold or allergy induced symptoms, whether by physiological reaction, by sensory effects on the skin of the user, or combinations thereof, as a result of usage of conventional tissue products would be highly desirable. Thereby also the length of rhinological discomfort and the amount of tissue product required by the user can be reduced. Another added benefit is a direct reduction of the time for transmitting viral or bacterial causes of such discomfort. This follows the well known medical principle that fast relief also reduces the contamination probability.

Accordingly, there is a need to provide a fibrous tissue exhibiting a physiological and/or sensory rhinological discomfort relieve.

Further, there is a need for providing such a solution in an efficient, safe, affordable way, especially by providing the discomfort relieve with high efficacy, e.g. by ensuring good transferability, long exposure to the discomfort relieve means without unacceptable loss of other important tissue attributes, such as absorbency, strength or softness of tissues.

SUMMARY OF THE INVENTION

In order to solve the issues related to the state of the art and advance cold relief technology, the present invention provides a fibrous tissue including fibers suitable for the intended use and a volatile rhinological effective composition. The composition is effective on human skin by either providing physiological or perceived sinus relief.

DETAILED DESCRIPTION OF THE INVENTION

The present invention provides a fibrous tissue adapted for use in tissue products such as facial tissues, bathroom tissues, toilet tissues and disposable handkerchiefs comprising a volatile rhinological effective composition. The tissue may also exhibit a high level of surface smoothness and softness, high absorbency, a high strength and a high bulkiness. The volatile rhinological effective composition may be provided as part of a lotion applied in discrete deposits to the external surface of the tissue or of the tissue product or otherwise, as desired.

Fibrous Tissue and Tissue Product

The terms "fibrous tissue" and "tissue" are referred to interchangeably herein and prominently includes tissue paper. Besides the fibers used in conventional tissue paper materials, which are substantially provided from cellulose in the form of wood pulp fibers and some papermaking additives, the fibrous tissue according to the present invention may comprise as well some, a substantial quantity, or even only fibers of a different nature. The fibers utilized for the present invention may include fibers derived from wood pulp. Other cellulose fibers, such as cotton linters, bagasse, etc., can be utilized and are intended to be within the scope of this invention. Non-cellulose fibers such as those including starch and other polysaccharides, synthetic fibers, such as rayon, polyethylene, and polypropylene fibers can also be utilized alone or in combination with natural cellulose fibers. One exemplary polyethylene fiber that can be utilized is Pulpex®, available from Hercules, Inc. (Wilmington, Del.). Applicable wood pulps include chemical pulps, such as Kraft, sulfite, and sulfate pulps, as well as mechanical pulps including, for example, groundwood, thermo-mechanical pulp and chemically modified thermo-mechanical pulp. In addition to such fibers, a tissue making furnish used to make tissue structures can have other components or materials added thereto as known in the art. The types of additives desirable will be dependent upon the particular end use of the tissue sheet contemplated. For example, in tissue products such as toilet tissue, bathroom tissue, facial tissues, disposable handkerchiefs and other similar products, high wet strength is generally a desirable attribute. Thus, it is often desirable to add to the tissue making furnish chemical substances known in the art as "wet strength" resins.

The present invention is particularly useful with tissue paper in general, including but not limited to conventionally felt-pressed tissue paper; high bulk pattern densified tissue paper; high bulk, un-compacted tissue paper and through-air dried tissue paper. Included in the tissue paper definition are dry laid substrates and nonwoven webs. The tissue paper can be of a homogenous or multi-layered construction. Tissue products made fibrous tissues can be of a single-ply or multi-ply construction. Exemplary suitable tissue products may have a basis weight of between about 10 g/m$^2$ and about 65 g/m$^2$, and density of about 0.6 g/cm$^3$ or less. The basis weight will typically be about 40 g/m$^2$ or less for facial tissues, and 60+/−10 g/m$^2$ for handkerchiefs and the density will typically be about 0.3 g/cc or less. For measuring the density of tissue paper see Column 13, lines 61-67, of U.S. Pat. No. 5,059,282 (Ampulski et al.), issued Oct. 22, 1991, which describes how the density of tissue paper is measured. Unless otherwise specified, all amounts and weights relative to the paper are on a dry basis.

The "tissue products" of this invention are the finished products such as facial tissues, bathroom tissues, toilet tissues and disposable made from one or multiple plies of the above described fibrous tissues. Each ply of a multiply product can be made of different material or can have been manufactured in different ways. As used herein, the term "single-ply tissue product" means that it is comprised of one ply of tissue; the ply can be substantially homogeneous in nature or it can be a multi-layered tissue paper web. As used herein, the term "multi-ply tissue product" means that it is comprised of more than one ply of tissue. The plies of a multi-ply tissue product can be substantially homogeneous in nature or they can be multi-layered tissues. Further, the plies can be of the same construction and content or include different materials or processing steps prior to their combination.

Rhinologically Active Compounds and Composition

Besides fibers suitable for the final intended use, the tissue comprises a volatile rhinological effective composition. The composition is reactive on human skin and/or mucus either by providing sinus relief such as in expectorants or decongestants, or at least provides the perception of a sinus relief, or both. The time it takes for the effect to be recognizable on average will depend on the individual using tissues according to the present invention. Usually individuals having sinusoidal discomfort will feel an effect after less than 6 hours of only using tissues according to the present invention. However, relief may be obtained in less time, such as, for example, less than 3 hours or less than one hour after use. It is hence clearly distinguishable from anti-bacterial or anti-viral substances, which may however be included if so desired.

Rhinologically active compounds are, for example, disclosed in PCT publication WO-A-02/41861 as 'Rhinologica', which cause a fresh and relieving sensation in the respiratory tract, especially in the nose and throat cavity and the sinus cavities. Such compounds are conventionally not provided in the chemical sense as a single specific compound, but often in the form of a composition with a liquid or solid carrier. Hence the reference to compounds in the following includes the reference to compositions unless otherwise noted. Depending how a rhinologically active compound is provided it will often be included in a quantity of about 0.5% to about 20% of the composition it is provided in, including e.g. lotion compositions as explained hereafter.

Compounds also considered according to the present invention, but only mentioned as prior art in WO-A-02/41861 are those compounds referred to as lower alkyl ethers of isobornane and bornane as well as 1,8 cineol. Further eucalyptol and pinocarvone, both present in eucalyptus have been mentioned as potentially providing anti-microbial effects in EP-A-104783.

According to the intended use the compounds disclosed in WO-A-02/41861 are all expected (and hence considered) as volatile since they are transported by air into the indicated cavities. Generally 'volatility' is considered to be present for substances having a liquid or sublimation vapour pressure of the pure substance at 20° C. of at least about 0.013 Pascal (0.0001 mmHg), but may be at least about 0.1 Pascal. Volatility of substances having very high efficacy according to the present invention can be significantly higher by a factor of 10, 100 or even a 1000. The Vapour pressure can be measured according to ASTM Standard E1194-01 of November 2001. Of course, a too high vapour pressure may be undesirable if it causes the active substance to vaporise so easily that it creates significant difficulties to prevent the active substance from depleting prior to use of the tissue on which it is carried.

One compound which has been found to work particularly well in the context of the present invention is 1,8-cineol (also known as eucalyptol), e.g. available from Sigma-Aldrich Chemie Gmbh Munich, Germany. This substance has in addition a scent sometimes considered to imply refreshing. In some cases if such a scent is not desired, masking the scent or reducing it by low quantities of the substance is possible to achieve an application having a non-detectable smell profile (according to the triangle sensory test) compared to compositions without the substance. Also encapsulation or chemical complexing has been considered useful in the context of the present invention. 1,8-cineol has a vapor pressure of about 9 Pascal at 20° C. and another suitable compound is menthyl methyl ether, which has considerably less scent than 1,8-cineol and has hence a larger acceptance spectrum for potential users. Menthyl methyl ether can either be synthesized according to conventional chemical synthesis procedures or can be obtained from Sigma-Aldrich Chemie Gmbh Munich, Germany, or Symrise GmbH in Holzminden Germany. Menthyl methyl ether has a vapor pressure which particularly qualifies it as a volatile compound for the present invention.

Cooling Sensate

According to the present invention the tissue may also comprise a cooling sensate able to convey a cold/fresh perception to the user of such tissue without actually creating a direct reduction of temperature on the skin.

By perception it is meant the result perceived by the nervous central system of a user, which is a multi-step process initiated by the stimulation of sensory therno receptors on/in the skin and/or mucosal surface of the wearer. More details on such receptors are available in literature. An example of reference on thermo-receptors is:" Thermal sensation and thermo-receptors in man" by Herbert Hensel, M D, published by Charles C. Thomas in 1982.

If a cooling sensate is provided, the tissue products of the present invention comprise an amount of the volatile cooling sensate sufficient to reach and stimulate the receptors in the areas of the skin and/or mucosal surfaces such that the desired perception is created. The amount of sensate in each product will vary as the degree and longevity of the sensation varies from sensate to sensate and based on the way the sensate is applied to the tissue incorporated in the product. In certain embodiments, sensates inan amount of at least about 0.005% of the tissue weight, or at least about 0.01% of the tissue weight have been found acceptable. If the sensate is incorporated with other materials, especially as a compound of a lotion on the tissue then amounts of at least 0.05% by weight of the lotion, about 0.1% by weight of the lotion have been found to work satisfactory. In some embodiments of the present invention the sensate can also be encapsulated, complexed or stabilized in other forms usual in the art.

The sensate for use herein is a volatile cooling sensate, which is able to stimulate thermo-receptors (i.e., hot or cold sensory receptors), without the need to create direct temperature change on the skin. The cooling sensate suitable for use herein include all cooling sensates being able to penetrate the skin barrier and for which the cooling effect (herein also referred to as freshness effect) is a physiological effect due to the direct action of the sensate on the nerve endings responsible for the detection of cold without the occurrence of temperature change. Due to the persistence of the stimuli a long lasting freshness/cooling sensation is delivered.

It is to be understood herein that the freshness/cooling sensation is personal to a given individual. This perception depends on the density of thermo-receptors on skin and on the skin thickness. Typically it is observed that the thinner the skin is the more intense is the cooling sensation. Without to be bound by any theory, it is believed that the thinner the skin is, the more rapid is the penetration of the cooling agent through the skin and higher is the absorption level thereof.

Studies performed on cooling agent activity have shown that four features of the molecular structure of the cooling agents are relevant to deliver a cooling sensation. Reference is made to H. R. Watson et al., Journal of the Society of Cosmetic Chemist, Vol. 29, p185-200, 1978 and all cooling sensate information disclosed therein.

A well known cooling sensate is menthol. Menthol is not preferably used herein as the cooling agent, although menthol is known to provide cooling sensation, it suffers the disadvantage of having a strong mint odor, being a known irritant to skin at high concentration and strongly sublimating at room temperature. In particular the high sublimation rate causes the problem that tissues comprising menthol either have a strong mint smell or if the smell is acceptable the majority of the menthol has already vaporized prior to use of the tissue (or the menthol was never present in an objectionable quantity).

Particularly well known cooling sensate agents include ketals, carboxamides, cyclohexyl derivatives and/or cyclohexanol derivatives. Such and other cooling sensates are described in detail e.g. in EP-A-1.250.940 and EP-A-1.250.941, U.S. Pat. Nos. 5,451,404, 5,266,592, DE-A-2.608.226, and DE-A-2.458.562.All of the cooling sensates disclosed in these references can of course be used in embodiments of the present invention, provided they are volatile, accepted as safe for use on human skin, and generally satisfy the criteria defined herein. A cooling sensate might be used alone or in combination with other sensates.

Exemplary suitable cooling sensates are: 2-Isopropyl-N,2,3-trimethylbutyramide, commercially available from e.g. Millennium Chemicals of Lyondell in Houston, Tex. USA, under the trade name WS-23, or from Qaroma, BAYTOWN, Tex. USA, under the trade name ICE 1000.This material has a vapor pressure of about 0.53 Pascal (equivalent to 0.004 mmHg at about 20° C.). Other suitable cooling sensate substances according to the present invention are the various isomers of Isopulegol or compositions of them, in particular the (−)-Isopulegol, commercially available from Takasago Deutschland GmbH, Duesseldorf, Germany under the trade name Coolact P.

If cooling sensates and rhinological effective compositions are combined for use in handkerchiefs their total beneficial effect (perceived and/or physiological) has been found to show a strong non linearity (synergy) in fighting cold and allergy symptoms of the respiratory systems. It is believed that one benefit provided increases the efficacy of the other benefit and vice-versa, thus leading to fast and unexpected relief.

Lotion and Application of the Lotion

A "lotion" is a composition added to the tissue in order to improve its softness and/or smoothness and has a smoothening effect when some of the lotion is transferred from the tissue to the user's skin upon use of the paper tissue article. The lotion may comprise tissue softening and/or debonding agents, emollients, immobilizing agents and mixtures thereof. Suitable softening and/or debonding agents include quaternary ammonium compounds, polysiloxanes, and mixtures thereof. Suitable emollients include propylene glycol, glycerine, triethylene glycol, spermaceti or other waxes, petrolatum, fatty acids, fatty alcohols and fatty alcohol ethers or esters having from 12 to 28 carbon atoms in their fatty acid chain, mineral oil, namely silicone oil e.g. dimethicone and isopropyl palmitat, and mixtures thereof. Suitable immobilizing agents include waxes, fatty alcohols, fatty acids, e.g. ceresin wax, microcrystalline wax, petroleum waxes, fisher tropsh waxes, paraffin waxes, stearyl alcohol and paraffins, polyhydroxy fatty acid esters, polyhydroxy fatty acid amides, and mixtures thereof. In most cases, the lotions contain at least one immobilizing agent and an emollient. Lotions can be emulsions or dispersions. Other optional components include perfumes, antibacterial actives, antiviral actives, disinfectants, pharmaceutical actives, film formers, deodorants, opacifiers, astringents, solvents and the like. Particular examples of lotion components according to the present invention include thymol, chamomile extracts, aloe vera, calendula officinalis.

According to the present invention the volatile rhinological composition can be incorporated into the lotion. This has the added advantage that the volatile rhinological composition is transferred to the skin in the region where the effect is mostly intended and when the tissue product is used as a handkerchief the volatility of the rhinological composition allows highly effective transport of the sensate to receptor sites of the mucous skin in the nasal cavity. According to the present invention the lotion can be the carrier for both the volatile rhinological composition and a cooling sensate. All of this can be provided independent of the lotion deposition on the fibrous tissue. However the more effective the lotion deposition for lotion transfer the more effective will the volatile rhinological composition perform as well.

In this context it is particularly preferred that the lotion comprising a rhineological effective composition and/or a cooling sensate has no olfactory disadvantage to the same lotion without the sensate. In other words there should not be a substantially different smell of the lotion due to the rhineological composition or sensate component. This is also referred to as subliminal usage of a cooling sensate and would allow quantifying how much of an otherwise objectionably smelling rhineological composition or cooling sensate could be used without causing such objection. This can be evaluated by triangular sensory smell analysis according to DIN 4120, of January 1995 when comparing tissue samples carrying the lotion with and without the cooling sensate. Of course such comparison requires proper setting according to DIN 10962 (requirements for sensor test rooms), education of the test individuals and recognition of standard compositions according to DIN 10961 and DIN 10964 as well as education of test individuals and ranking of intensity differences (including menthol, camphor evaluations). Comparisons resulting in insignificant differences (or even identity) will be acceptable in the context of the present invention, however also comparisons where a deviation of less than 20% of the ranking scale can be found are considered acceptable and would usually be referred to as slightly recognizable smell. Compositions comprising rhinological compositions and/or cooling sensates causing no more than such slightly recognizable smell detection are considered not detectible by smell analysis for the purpose of the present invention.

A "lotion deposit" (or "deposit") is an area of relatively high lotion basis weight. A deposit is defined as an area of tissue comprising lotion with a local lotion basis weight of at least about 10 g/sqm. Areas on the tissue with lower local basis weights are not part of a deposit. The local basis weight on the tissue is measured as described hereafter.

"Lotion basis weight of the deposits" is the basis weight of lotion, expressed in grams per square meter, within the region of the deposits of lotion on the tissue. This takes only into account the area of the deposits and the amount of lotion within the deposits and is an average value of the deposits measured. The lotion basis weight of the deposits is measured by the method described hereafter. "Lotion basis weight of the tissue" is the overall basis weight of lotion, expressed in grams per square meter, of lotion on the tissue. The basis weight can be measured by standard methods, e.g. solvent extraction, or calculated from the process conditions (total amount of lotion deposited on the tissue divided by the total area of the tissue).

"Size of deposits" is the average size of the deposits of lotion on the tissue, as measured by the method described thereafter.

"Area of tissue affected by lotion" is an area with a local lotion basis weight of more than about 3 g/sqm as determined by the method described herein.

It is desirable to provide a tissue with a lotion able to be transferred easily onto skin during use. The selection of the distribution of the lotion on the tissue, as a multitude of discrete deposits, can enhance the transferability of the lotion from the tissue onto the skin of the user. The higher the basis weight of the lotion within the deposits the higher the availability for transfer to skin upon use. Indeed, with a relatively high local concentration of lotion in discrete deposits, a relatively low amount of lotion remains stuck on the tissue. It is hence desirable to provide discrete deposits with a high local concentration of the lotion in the deposits and a relatively low basis weight of lotion of the tissue. In certain embodiments of the invention, the lotion basis weight of the deposits is at least about 11 g/sqm, about 13 g/sqm, about 15 g/sqm, about 17 g/sqm, about 20 g/sqm, about 25 g/sqm or at least about 30 g/sqm, while the basis weight of lotion of the tissue is equal or less than about 9 g/sqm, less than about 6 g/sqm, less than about 4.5 g/sqm, about 3.0 g/sqm or less than about 2 g/sqm.

The application of the lotion can be done via the use of rotating applicator surfaces from which the lotion is expulsed to impact a fibrous tissue. The temperature of the rotating surface should match the characteristics of the lotion, in order to ensure balancing two phenomena. First, the expulsion disperses the lotion into a stream or cloud of droplets. The size and density of the stream of droplets can be controlled by temperature at which, the lotion leaves the rotating applicator surface. Second, the droplets are expulsed in a liquid or quasi-liquid form and are in a solid or quasi-solid form when they impacted the tissue to prevent their penetration into and absorption within the tissue. The droplets have a tendency to stay immobilized at the surface of the tissue supporting the desired high transferability of the lotion. Examples of rotating applicator units capable to deliver discrete deposits of lotion are described in WO-A-02/34519 or WO-A-02/234520.A commercially available rotary spray application system RFT-Compact-III with applicator heads for the tissue and textile industry are available from Weitmann & Konrad GmbH & Co KG, Leinfelden-Echterdingen, Germany.

EXAMPLE

The following composition (given in weight percent) has been found to be effective on disposable tissues and handkerchiefs, etc. It is hypothesized that the lotion is particularly suited to provide the desired lotion deposits and distribution. Also the combination of volatile rhinological composition and the cooling sensate provides significant perception of decongestion when used by individuals having a cold or other rhinological discomfort.

| | |
|---|---|
| Stearyl Alcohol CO1897 * | 39.2% |
| Petrolatum Snowwhite V28EP ** | 29.5% |
| Mineral oil Carnation ** | 29.5% |
| 2-Isopropyl-N,2,3-trimethylbutyramide (WS23)*** | 0.3% |
| Menthyl methyl ether**** | 1.5% |

* Available from Procter&Gamble Chemicals, Cincinnati, USA
** Available from Crompton Corporation
***Available from Millennium Specialty Chemicals
****Available from Symrise GmbH The above formulation is applied equally to both outer surfaces of a tissue paper product. Total add-on level is about 6 g/sqm, about 3 g on each outer surface, using a rotary surface application method to create discrete lotion deposits. The paper tissue used is a conventional wet pressed, homogeneous, dry creped tissue essentially of wood pulp fibers with a basis weight of about 15.4 g/sqm. The wood pulp fibers have a composition of about 40% Northern Softwood Kraft fibers and 60% Eucalyptus fibers. Following the papermaking, four sheets of paper are combined in an off line combining operation and rewound into a parent roll. The pre-combined 4-ply parent roll is subsequently converted into a 4-ply tissue product. The 4-ply parent roll is unwound and subjected to calendaring between two smooth steel calender rolls followed by high pressure embossing to achieve ply bonding. The majority of the tissue paper remains unaffected by the high pressure embossing. Finally the tissue is cut in machine direction, followed by cutting in cross direction into sheets of approximately 21 cm×21 cm, folded, stacked into stacks of 9 handkerchiefs and packed into individual handkerchief pocket packs. The 4-ply paper tissue product obtained by the above described process has a basis weight of approximately 60 g/sqm (not including lotion), a thickness of 0.27 mm, a machine direction strength of 1280 g/2.54 cm, a cross direction strength of 610 g/2.54 cm, and a wet burst of about 200 g. The tissue includes a wet strength agent and a dry strength agent.

The product was then submitted to a consumer use test together with a comparative tissue product treated with the same lotion but without the volatile rhinological composition and without the cooling sensate (increased percentages for the other ingredients) with the same add-on level on the tissue. A significantly higher proportion of panelists claimed to perceive a refreshed feeling and sinus relief as well as being able to breathe more freely when using the handkerchiefs of this example compared to the comparative product.

Test Methods:

Lotion basis weight of the tissue, as an average lotion basis weight can either be determined by calculating the basis weight from material consumption of lotion and surface are of tissue. Alternatively, a solvent extraction method can be used to measure the lotion basis weight of the tissue in the absence of knowing material consumption values or to reconfirm that no substantial amounts of lotion are lost during processing. In this method, a representative sample of about 2 g of the lotion treated tissue is used. First, the surface area of the sample is determined. Then the lotion is extracted by Accellerated Solvent Extraction (ASE) using a model ASE 200, available from Dionex Corp., USA. The conditions should be such that all lotion ingredients are extracted. The solvent is evaporated and the residue is determined gravimetrically. The lotion basis weight of the tissue is then calculated as weight of the extract in grams divided by the surface area of the sample.

Care should be taken when selecting the solvent for this method to be substantially able to dissolve all components of the lotion. In cases where the lotion is insufficiently soluble in this solvent to perform a quantitative extraction, an alternative solvent has to be chosen that is suitable to quantitatively extract the lotion.

Method for Quantifying the Lotion Basis Weight of the Deposits:

This method allows determination of local lotion basis weight (LLBW), lotion basis weight of the sample (LBWS), lotion basis weight of the deposits (LBWD), Area affected by deposits (AAD), Area affected by lotion (AAL), and average deposit size (ADS).

The local lotion basis weight is determined by scanning IR/NIR (infrared or near infrared) spectroscopy in transmission mode (absorption spectroscopy) using a Perkin Elmer Spectrum Spotlight 300 instrument in combination with Spotlight software version 1.1.0 B38.

The following procedure is applicable to lotions containing linear hydrocarbon components of repeated—($CH_2$)—units. Adaptation of the procedure may become necessary if the lotion is composed mostly or entirely of other materials. Such adaptations will depend on the lotion composition and will usually be apparent to those skilled in the art.

The measurements are done with samples representative for the tissue. A 5×5 mm sample (or larger) is placed on the sample holder, which is mounted on a XY table and the spectral area used for analysis is scanned at a spatial resolution of 25 µm in both x and y dimension. For the analysis of materials containing linear chains of—$CH_2$- groups the region between 4000 cm-1 and 4500 cm-1 is scanned and the range between 4296 cm-1 (W1) and 4368 cm-1 (W2) is used for analysis. At least 16 scans are taken at a resolution of 1 cm-1. If more than 16 scans are used, care needs to be taken that the sample does not change structure as a result of heating up.

Next, a map of the local basis weight of the sample is generated. The integrated absorption between W2 and W1 and above a sloping linear baseline is determined for each pixel of 25 µm×25 µm using the ChemiMap menu of the software. The baseline is defined by the absorbency at W1 and W2. The two base points option is chosen in the ChemiMap menu of the software and set at W1 and W2. Start and end point of the integration are also set at W1 and W2. The scaling factor is set to a value V1 which is defined as: V1=F*DW where F is the factor described below and DW=W2−W1 is the delta in wave numbers between the upper (W2) and the lower (W1) wave number in $cm^{-1}$.

The scaling with the factor DW transforms the average absorbance above the baseline within the wave number range W1 to W2 into an integrated absorption above the baseline. The factor F translates the integrated absorption into local basis weight in g/sqm.

The file, which is generated with the ChemiMap command, contains the local basis weight for each pixel of 25 µm×25 µm in area. The file is saved as a text file (.txt format) and also as a bitmap (.bmp format) in 8 bit grey scale format. The text file is imported into EXCEL and the first row and first column are removed (they do not contain image data, but position data). The resulting data are representing the array of pixels of local basis weight in g/sqm. The maximum (MaxLBW) and minimum (MinLBW) value, as well as the average (AvgLBW) of the whole dataset is calculated in EXCEL.

The bitmap file (.bmp file) is imported into AnalySIS image analysis software for further processing (Analysis Pro version 3.1 (build 508), available from Soft Imaging GmbH, Germany). The imported grey scale file is still in RGB format with all three color channels set equal (in 8 bit resolution). In AnalySIS the file is color separated to extract one of the three identical color channels (red). The resulting file is now scaled from G=0 to G=255, G=0 representing the minimum value (MinLBW) of the original spotlight data and 255 representing the maximum value (MaxLBW) of the original spotlight data. The image is calibrated in x-y by setting the pixel size in x and y dimension to match the original sample. The image is rescaled in z-direction to display the local basis weight values in g/sqm but all calculations within AnalySIS have to be made in the G=0 to G=255 scale. The G values can be easily transformed into local lotion basis weight numbers by the following relationship:

LLBW=$A$*($G$+OFFSET), where $A$=(MaxLBW−MinLBW)/255 and

OFFSET=(255*MinLBW)/(MaxLBW−MinLBW)

The G values can be easily transformed into local lotion basis weight numbers (LLBW) by the following relationship: G=(LLBW/A)−OFFSET Calculation of the lotion basis weight of the deposits: The average value of all local lotion basis weight data points above 10 g/sqm can be calculated from the EXCEL data file.

The area of tissue affected by lotion is calculated in Analysis by setting a lower threshold at the G value equivalent to 3 g/sqm and calculating the area above that threshold. The setting "holes not filled" is used. The area of the deposits is similarly determined by setting the threshold at a G value equivalent to 10 g/sqm (10 g/sqm equals G=10/A−OFFSET).

If deposits are defined to have a certain minimum and/or maximum, area is set as a filter. The area percentage of deposits larger than a certain area is calculated by dividing the area of the deposits calculated without area filter, divided by the area of the deposits calculated with area filter.

The factor F to convert integrated absorption values into local lotion basis weight values is determined by the following procedure: A representative set of calibration samples of known average lotion basis weight is scanned in the spectral range used for the analysis as described above and analyzed for integrated peak area between W1 and W2 (4296 cm-1 and 4368 cm-1 for mostly hydrocarbon like materials). The integrated peak area is obtained from the procedure above if the factor F is set equal to 1. The dataset is then imported to EXCEL and the average pixel value of this dataset is calculated. As the factor F was set equal to 1 this value is equal to the mean integrated peak area (AIPA) of the sample in the wave number range W1 to W2. The factor F is then calculated as F=1/slope of a linear least square fit through the origin of the plot of AIPA vs. average lotion basis weight of the sample. Calibration samples to determine the factor F can either be prepared or an existing lotioned sample can be used. If an existing sample is used the lotion basis weight can be determined by extraction. An example for such a procedure is given below. Examples for how the factor F is determined by analyzing an existing sample (market product) and by preparing calibration samples is also given below. It is important, that the absorbency in the wavelength range used for analysis should never exceed about 1 to ensure a linear correlation between the infrared signal and the local lotion basis weight Determination of Factor F by Preparing Calibration Samples:

A suitable piece of the substrate of known area, weight and basis weight is evenly treated with lotion, preferably by evenly spraying the molten lotion onto the tissue. A suitable type of equipment is a hot wax cartridge spray gun type MK-DUO Line Art. No. 140101, available from MK Heißwachstechnik GmbH, Aichach, Germany. After the application, the lotion is equilibrated in the sheet by placing the sample in an oven at a temperature of about 10° C. above the mp (or at a temperature suitable to allow for sufficient equilibration of the lotion in the sheet). For relatively low viscosity samples equilibration for about an hour is sufficient. The sample is then cooled down to room temperature and equilibrated for moisture content at 23° C. (+−1° C.) and 50% (+−2%) relative humidity and weighed again. The lotion basis weight of that sample [in g/sqm] is then calculated as (sample weight after lotion treatment [in grams]—sample weight before lotion treatment [in grams]) divided by area of the sample [in sqm]. The samples are then analyzed by the procedure described above to determine the factor F. Preferably, calibration samples are prepared in a range of lotion basis weights that include the range to be measured.

Determination of Factor F for a market product: The basis weight of the sample is determined by a standard procedure. The sample is then analyzed by the procedure described above for the average integrated peak area between 4296 cm-1 and 4368 cm-1. The sample is then extracted by the procedure described below to determine the lotion add-on. The Factor F is then calculated as Factor F=lotion basis weight [g/sqm]/average integrated peak area If the lotion does not contain a sufficient amount of linear hydrocarbon like material, or the substrate contains materials that do not allow for a quantification of lotion between 4296 cm-1 and 4368 cm-1, a different wave number range in the infrared or near infrared range has to be identified that is suitable to quantify the lotion by IR spectroscopy. Any wave number range with a linear correlation between integrated absorption coefficient above base line and lotion basis weight can be used. If more than one possible wave number range can be identified, the range with the best signal to noise ratio is used. Whenever the lotion is based on linear hydrocarbon like materials with CH2 groups the absorption band between 4296 cm-1 and 4368 cm-1 should be used.

All documents cited in the Detailed Description of the Invention are, in relevant part, incorporated by reference herein; the citation of any document is not to be construed as an admission that it is prior art with respect to the present invention. To the extent that any meaning or definition of the term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:
1. A fibrous tissue comprising:
fibers suitable for the intended use;
a volatile rhinological effective composition comprising menthyl methyl ether, said composition being effective on human skin by either providing physiological or perceived sinus relief;
wherein said tissue further comprises a transferable lotion in addition to the volatile rhinological effective composition;
wherein said lotion is present in substantially discrete deposits on at least one of said external surfaces and said lotion basis weight in said deposits is at least about 11 g/sqm; and
wherein said tissue further comprises a cooling sensate in the amount of at least about 0.005% by weight of said tissue.

2. The tissue of claim 1 wherein said volatile rhinological effective composition is disposed in a transferable lotion composition capable of transferring to skin when the tissue, comes into contact with skin.

3. The tissue of claim 1 having two external surfaces and wherein said lotion is present in substantially discrete deposits on at least one of said external surfaces and said lotion basis weight in said deposits is at least about 15 g/sqm.

4. The tissue of claim 1 having two external surfaces and wherein said lotion is present in substantially discrete deposits on at least one of said external surfaces and said lotion basis weight in said deposits is at least about 25 g/sqm.

5. The tissue of claim 1 having two external surfaces and wherein said lotion is present in substantially discrete deposits on at least one of said external surfaces and said basis weight of lotion on the tissue is equal to or less than about 9 g/sqm.

6. The tissue of claim 1 wherein there are at least two discrete deposits per square cm of the external surface on which the lotion is disposed.

7. The tissue of claim 1 wherein said tissue comprises at least about 50% of cellulose fibers by weight of said fibers of said tissue.

8. The tissue of claim 1 wherein said tissue comprises at least about 80% of cellulose fibers by weight of said fibers of said tissue.

9. The tissue of claim 1 wherein said tissue comprises at least about 90% of cellulose fibers by weight of said fibers of said tissue.

10. The tissue of claim 1 wherein said tissue comprises cooling sensate in the amount of at least 0.05% by weight of said tissue.

11. A fibrous tissue comprising:
fibers suitable for the intended use;
a volatile rhinological effective composition comprising menthyl methyl ether, said composition being effective on human skin by either providing physiological or perceived sinus relief;
wherein said tissue further comprises a transferable lotion in addition to the volatile rhinological effective composition;
wherein said lotion is present in substantially discrete deposits on at least one of said external surfaces and said lotion basis weight in said deposits is less than about 6 g/sqm; and
wherein said tissue further comprises a cooling sensate in the amount of at least about 0.01% by weight of said tissue.

12. The tissue of claim 11 having two external surfaces and wherein said lotion is present in substantially discrete deposits on at least one of said external surfaces and said basis weight of lotion on the tissue is equal to or less than about 3 g/sqm.

* * * * *